United States Patent
Daneshvar

[19]

[11] Patent Number: 5,904,701
[45] Date of Patent: May 18, 1999

[54] DEVICE FOR AIDING PROCEDURAL AND THERAPEUTIC INTERVENTIONS OF THE GASTROINTESTINAL TRACT

[76] Inventor: Yousef Daneshvar, 21459 Woodfarm, Northville, Mich. 48167

[21] Appl. No.: 08/194,905

[22] Filed: Feb. 14, 1994

[51] Int. Cl.$^6$ .................................................. A61M 29/00
[52] U.S. Cl. .................. 606/192; 606/196; 128/DIG. 25
[58] Field of Search ...................................... 606/192, 194, 606/196; 128/DIG. 25

[56] References Cited

U.S. PATENT DOCUMENTS

| | | | |
|---|---|---|---|
| 3,154,077 | 10/1964 | Cannon | 606/192 |
| 3,797,478 | 3/1974 | Walsh et al. | 128/DIG. 25 |
| 3,903,893 | 9/1975 | Scheer | 606/196 |
| 4,291,687 | 9/1981 | Sinnreich | 606/192 |
| 4,555,242 | 11/1985 | Saudagar | 606/192 |
| 4,686,985 | 8/1987 | Lottick | 606/192 |
| 4,932,959 | 6/1990 | Horzewski et al. | 606/194 |
| 5,002,531 | 3/1991 | Bonzel | 606/194 |
| 5,108,370 | 4/1992 | Walinsky | 606/194 |
| 5,226,888 | 7/1993 | Arney | 606/194 |

*Primary Examiner*—Michael Buiz
*Assistant Examiner*—Nancy Connolly Mulcare

[57] ABSTRACT

Balloons are shaped and adapted for use in hollow body orifices. The balloons can be inflated and expanded within the body cavity in such a way as to prevent bleeding in the area, to apply pressure to the area or to allow application of medicine in the region. Each of these application can be performexd without disturbing bodily functioning in the area of application.

4 Claims, 11 Drawing Sheets

DEVICE FOR AIDING PROCEDURAL AND THERAPEUTIC INTERVENTIONS OF THE GASTROINTESTINAL TRACT

THE BACKGROUND OF THIS INVENTION

The bleeding in human beings is common and many times it happens in a hollow part of the body such as the gastrointestinal system, nose or trachea. Therefore during treatment it is important not to prevent the function of such hollow areas since it will disturb the function of the body and cause suffering, complications or even the death of the person. This unit is made to allow problems in such hollow areas to be taken care of without disturbing their function to a significant degree. This unit also has other uses such as to allow to visualization of the gastro-intestinal system during endoscopy, etc.

THE BRIEF EXPLANATION OF INVENTION

This invention deals with making a special type of balloons that will be shaped and made to be used in hollow areas or parts of body and for them to be expanded to prevent bleeding or to apply a medication or pressure while having an opening to allow the passage of the materials in that area to occur and the person not to suffer from blockage in the area or to be subject to other complications.

THE FIGURES

THE DETAILED EXPLANATIONS OF THE FIGURES

Figure 1:
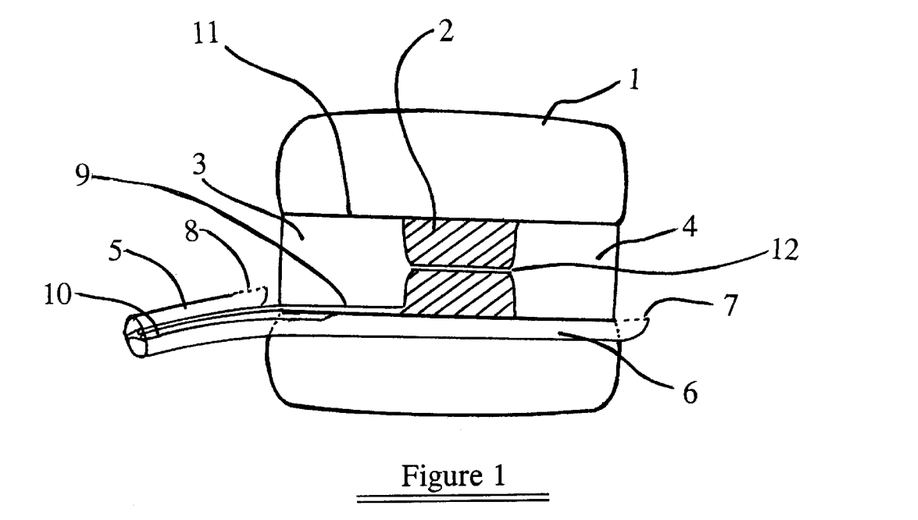
FIG. 1. This shows a cross cut view of a prototype unit.

FIG. 1. This figure shows a cross cut view of a prototype of this unit which is basically designed to be used in colon however it represents the general idea as well. In this figure the unit is shown in inflated condition. In this view the outer balloon is shown as well as a the cross cut (11) of the central tube that will give body to the unit and has the inner balloon in inflated state. This figure also shows the cross cuts of the tubings that are for fluid injection. One tube (6) takes the water to the area above the balloon and the other one (5) to the area below the balloon. Two inflation tubing are shown as well. In this figure the body of the main outer balloon is shown at 1 and the smaller inner balloon is shown with dashed area at 2. The central tubing C that will give body to the unit is shown at 11 and the part of this tubing before the inner tubing will be shown at 3 and the part that is above the inner tubing is shown at 4. The outer balloon has an inflation tube marked at 10 and the inner balloon will be inflated via the inflation tubing at 9. No 12 shows the tiny space in the center of the inner balloon which naturally will vary based on the amount of the air in the balloon 2. No 6 shows a tubing that may be used for flushing the area above the balloon and no 7 shows its opening. No 5 shows a tubing that may be used for flushing the area below the balloon. No 8 shows the opening of this tubing. The tubing of this unit will have markings to allow the position of the unit to be verified. Also some units will have bulbs to allow the light to guide about knowing the position of the unit in the bowel.

Figure 2:
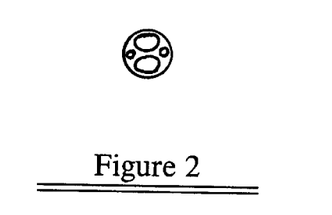
FIG. 2. This shows the cross cut view of the collection of tubings.

FIG. 2. This figure shows the cross cut view of the collection of tubings. In this view two large tubes are shown and are for suctioning of water or injection of fluid and there are also two small tubing that are for inflation of the balloons. A protective cover covers this collection.

Figure 3:
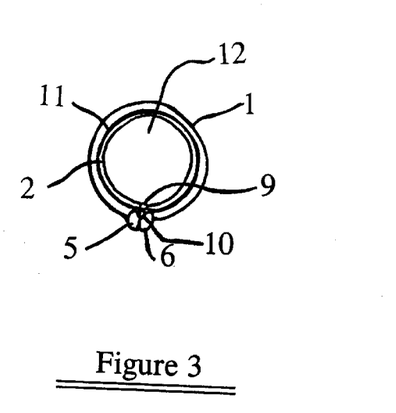
FIG. 3. This shows the horizontal cross cut view of the unit in deflated condition.

FIG. 3. This figure shows the horizontal cross cut view of the unit when it is in deflated condition. In this figure the outer balloon is shown over the circular central tubing C, and the inner balloon is shown at the inner surface of the central hard plastic tubing C. In the lower edge the cross cut of the tubing is also shown. In this figure again the body of the main outer balloon is shown at 1 and the smaller inner balloon is shown at 2. And the central tubing C at 11. The inflation tube marked at 10 will allow inflation of the outer balloon and the inflation tubing of 9 will allow the inflation of the inner balloon to occur. No 6 shows the cross cut of a tubing that may be used for flushing the area above the balloon and no 5 shows the cross cut of a tubing that may be used for flushing the area below the balloon. No 12 shows the opening inside the inner balloon.

Figure 4:
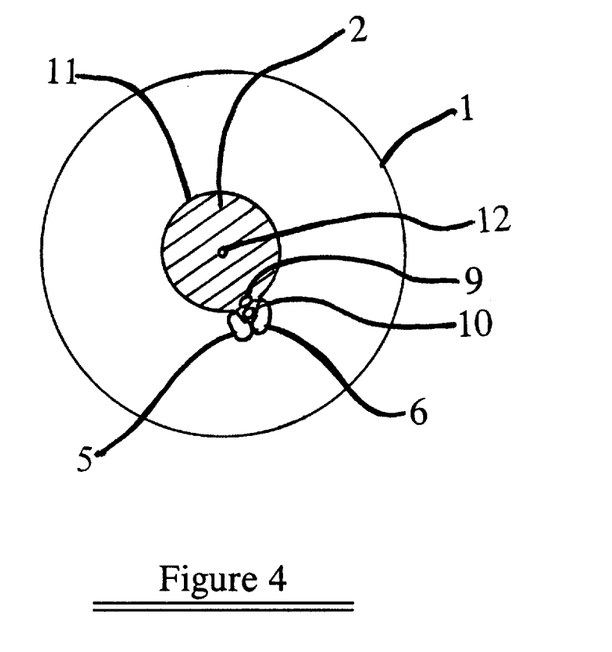
FIG. 4. This shows the horizontal cross cut view of the unit in inflated condition.

FIG. 4. This figure shows the horizontal cross cut view of the unit when it is in inflated position as shown in previous figure of 1. In this figure the outer balloon is shown over the hard plastic part, and the inner balloon is shown at the inner side of the hard plastic tubing C. And in the lower corner the cross cut of the tubing is also shown. In this figure the body of the main outer balloon is marked at 1 and the smaller inner balloon is shown with a dashed area at 2. And the central tubing C at 11. The inflation tubings of 9 and 10 are shown as well as the open tubings of no 5 and 6. No 12 shows the opening inside the inner balloon.

Figure 5:
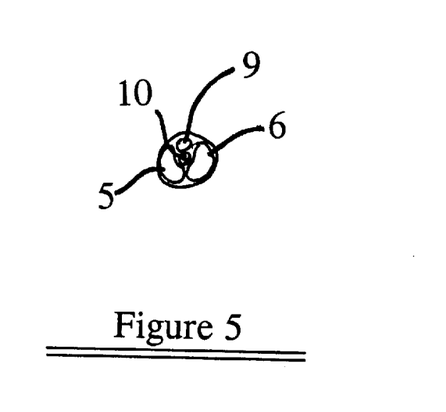
FIG. 5. This shows the horizontal cross cut view of the tubing of this unit.

FIG. 5. This figure shows the horizontal cross cut view of the tubing of this unit. In this model the inflation tubings of 9 & 10 as well as the open tubings of 5 and 6 are shown as well.

Figure 6:
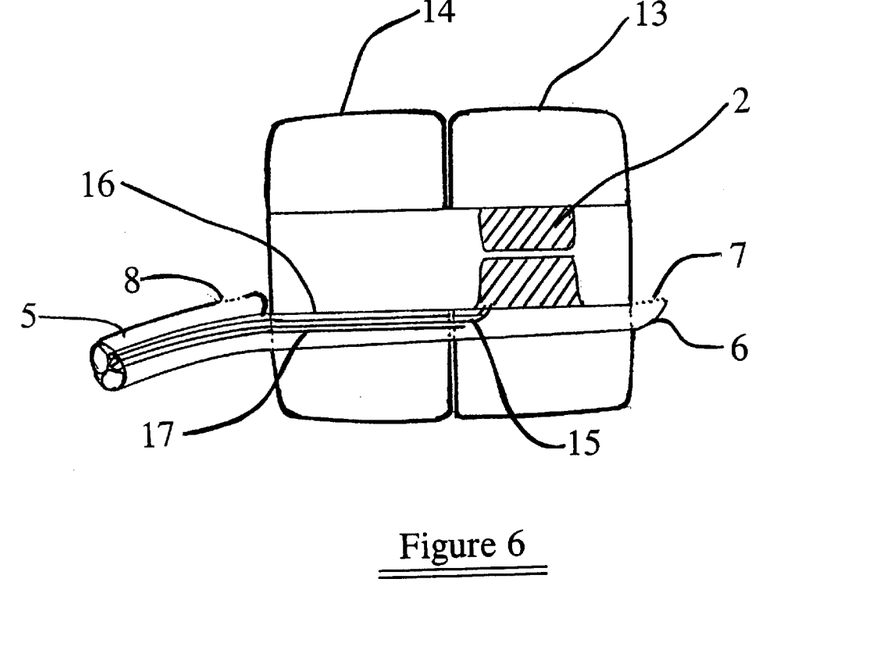
FIG. 6. This shows a cross cut of a unit that has two balloons 13 and 14.

FIG. 6. This figure is a cross cut view of a prototype unit similar to the one shown in previous figure of 1. Except in this unit the outer balloon is made from combinations of two balloons 13 and 14 which are independent from each other and having two different inflation ports. This will allow simultaneous or the intermittent inflation of these balloon to occur. Also this figure shows that the inner balloon 2 may be placed in different area or part of the central tubing as well. In this figure the unit is shown in inflated condition. In this view the outer balloons are shown at 13 & 14 the balloon 11 will be inflated by a special inflation tubing shown at 16 and the balloon 14 will be inflated by another inflation tubing here shown at 17. The inflation port for the inner tubing is marked at 15. Here again the tubings (5) and (6) that are for fluid injection or other purposes are shown. In the left end these tubings are bounded together to make one single tubing for easier handling.

Figure 7:
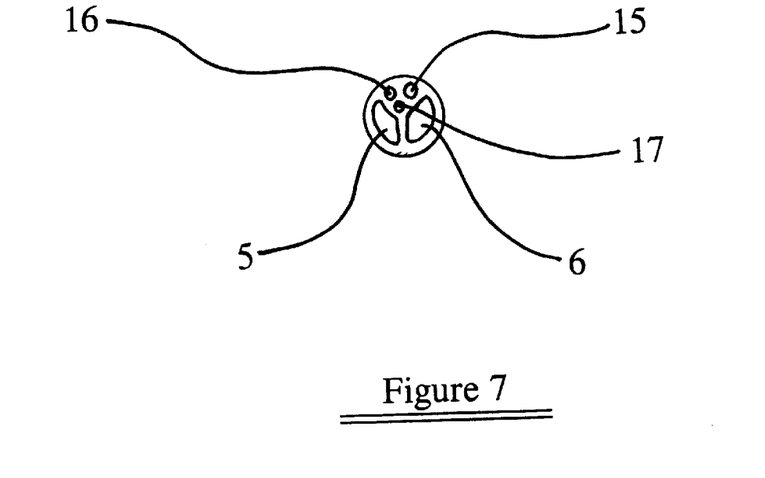
FIG. 7. This shows the cross cut of the collection of the tubings

FIG. 7. This figure shows the cross cut view of the collection of the tubings which are bound together for making a single unit for better handling. In this view the cross cuts of two large tubings of 5 and 6 are shown as well as the cross cut view of inflation tubing of 15, 16, and 17.

Figure 8:
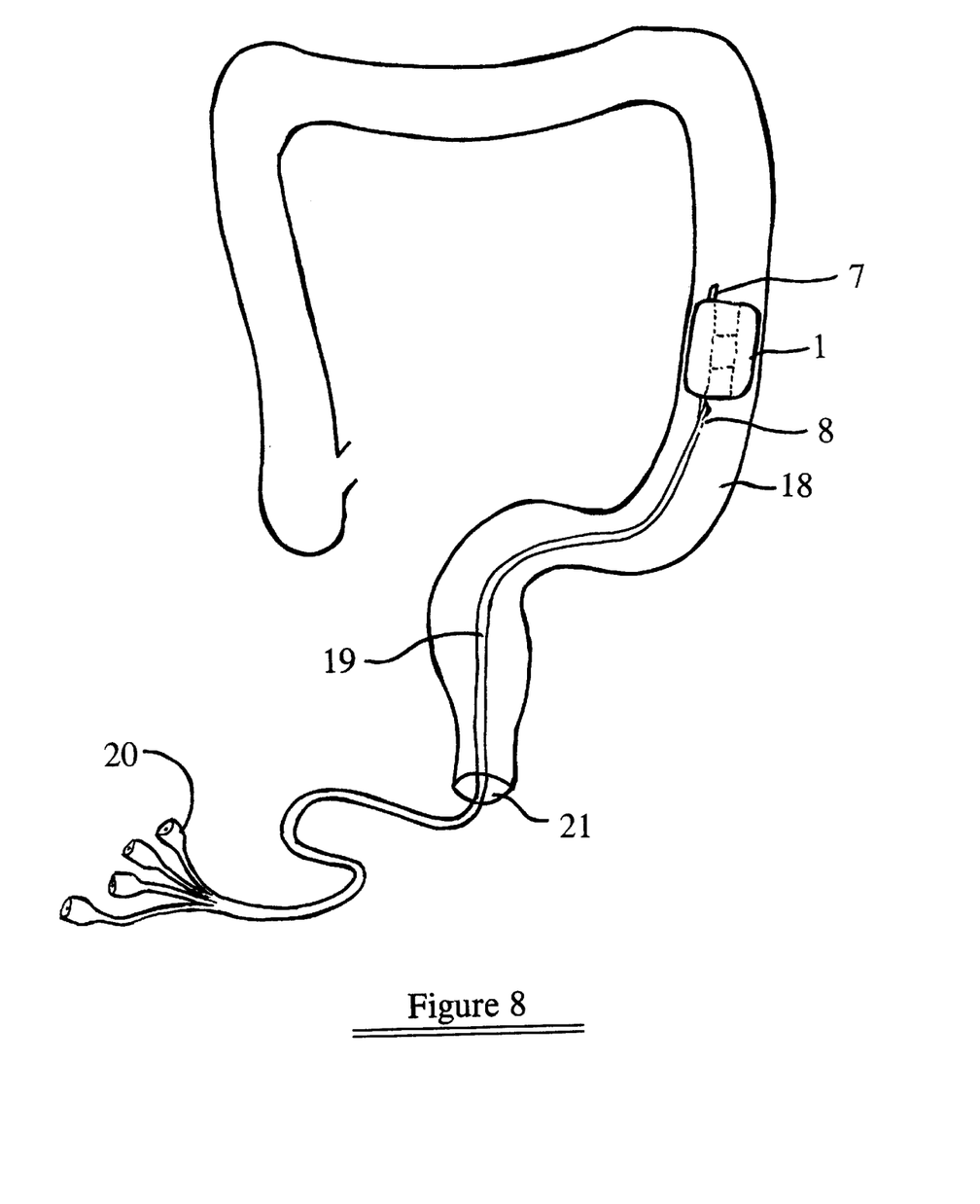
FIG. 8. This shows how this unit can be placed in the colon

FIG. 8. This figure is a schematic view to show how this unit can be placed in the colon to be functional. In this view the left side of the colon is shown at 18 with anal opening at 21. The balloon 1 is in place and the opening of its tubing of 7 and 8 are also marked. The main body of tubing coming from the balloon is shown at 19 and it continues to come along the colon to end in 4 endings that are properly made to allow inflation of the balloons to be done as well as flushing the area as well. One of such endings is shown at 20. Proper valves will be used in these endings.

Figure 9:
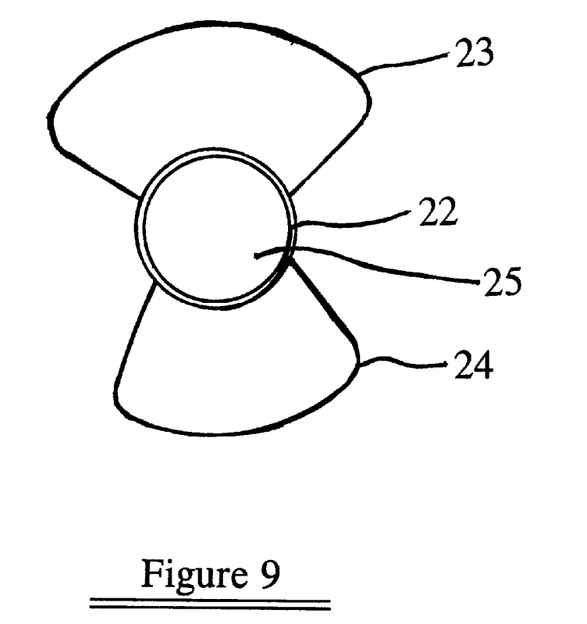
FIG. 9. This shows cross cut of a unit made from combinations of two balloons

FIG. 9. This figure is a cross cut view of another prototype unit similar to the one shown in previous figure of 1. Except in this unit the outer balloon is made from combinations of two balloons which can be connected or independent from each other as far as inflation is concerned. This model is to allow only some parts of the area to be pressed while the other area which is between these two balloons would not be affected. In this figure the unit is shown in inflated condition, and the outer balloons are shown at 23 & 24 the central tube C which gives body to the unit is marked at 22 and the opening of the inner tubing is shown at 25.

Figure 9A:
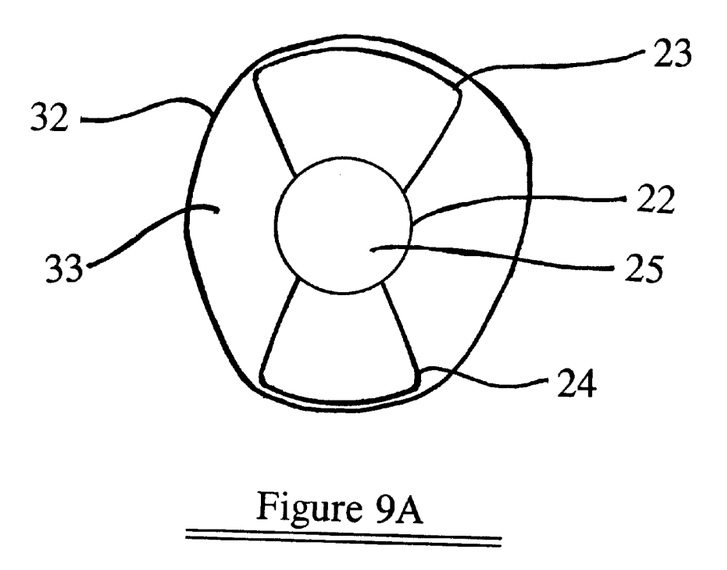
FIG. 9A. This shows a unit shown in FIG. 9 inside the colon.

FIG. 9A. This figure is a schematic cross cut view of an area of the colon which has a unit similar to the one shown in previous figure of 9 inside it. This figure is to illustrate how such a unit may function. In this view the body of the colon is shown at 32 and the unit is in its center. In this figure the unit is shown in inflated condition, and the outer balloons are shown at 23 & 24 the central tube C is marked at 22 and the opening of the inner tubing is shown at 25. The open area between the wall of the colon and the body of the unit is marked at 33 that will allow passages of the waste material to be done and also the pressure to the wall to be limited to the areas that are needed. Importantly although these units are mentioned about the colon however this idea may be also used in any other part of the body that they may be applied.

Figure 10:
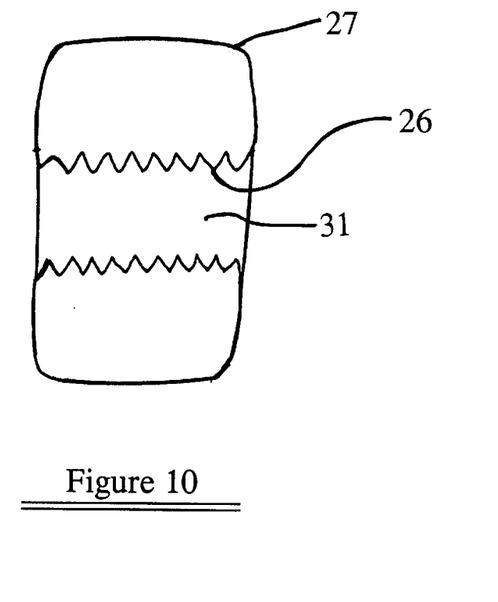
FIG. 10. This shows a model that its central tubing C can bend.

FIG. 10. This figure is a cross cut view of another prototype unit similar to the one shown in previous figure of 1. Except in this unit the central tubing C here marked at 26 will have a design to allow it to be bent without losing its function. For this reason here it is shown to have a wall like the wall of accordion that will allow bending to occur. In this figure the body of the outer balloon is shown at 27 and the opening in center is shown at 31.

Figure 11:
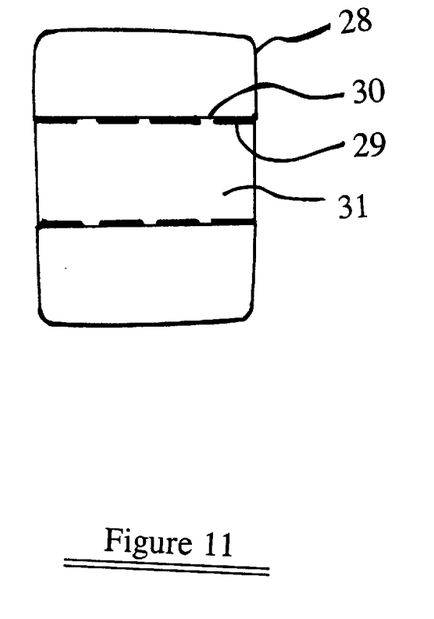
FIG. 11. This shows a unit that its central tubing C is made from combinations of separate parts.

FIG. 11. This figure is a cross cut view of another prototype unit similar to the one shown in previous figure of 1. Except in this unit again the central tubing C is made with a design to allow it to be bent without losing its function. For this reason here this part is made from combinations of separate parts that are connected to each other and the balloon and will allow bending to occur. In this figure one of the pieces of the central tube is shown at 29 the body of the outer balloon is shown at 28. The part of the balloon in between these pieces at 30 and the opening in center is shown at 31.

Figure 12:
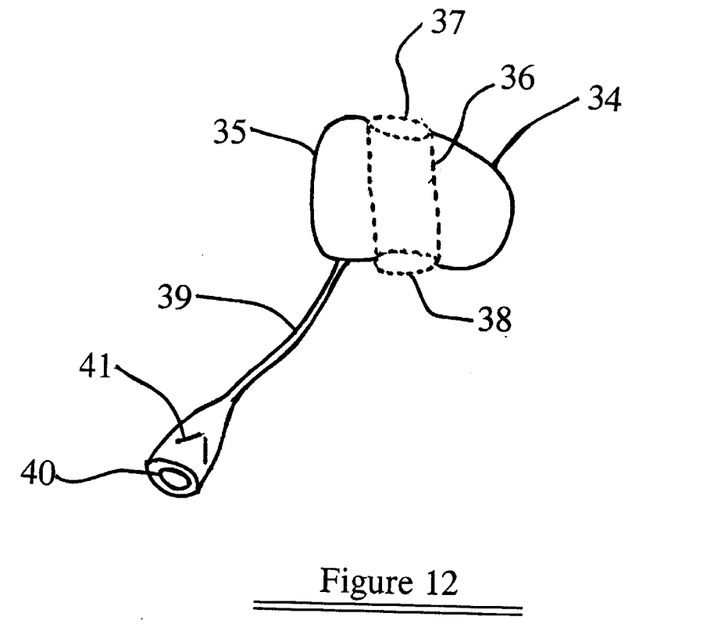
FIG. 12. This shows a nasal unit for the front part of the nose.

FIG. 12. This figure shows a prototype of a nasal unit that is designed to be used in the nasal bleeding. This unit will be basically made from a soft balloon that has an open center that will allow the motion of the air to occur. The balloon itself will be made from a soft plastic that will assume the shape of the space in front of the lower nasal area and will fill it after inflation. This unit also has an inflation port that will allow it to be inflated, and a valve that will allow it to be closed after inflation. In this figure the front of the body is shown at 34 and its rear side 35. The central tubing of this unit will have a rigid body so that it will not collapse after inflation of the balloon and is shown at dotted line of 36. This central tube 36 has an opening in the top shown at 37 and one in the bottom shown at 38. The inflation port is shown at 39 and the tip of this inflation port is shown at 40 with a valve marked at 41. The nature of this valve may be of any kind as well as to allow it to be inflated with a syringe and to be closed after the syringe is removed. In practice the outer surface of such a unit will be covered with a local anesthetic ointment and kept sterile inside a plastic cover ready to be used so that at the time of use it will be ready to be placed and also to numb the area quickly to prevent from pain.

Figure 13:
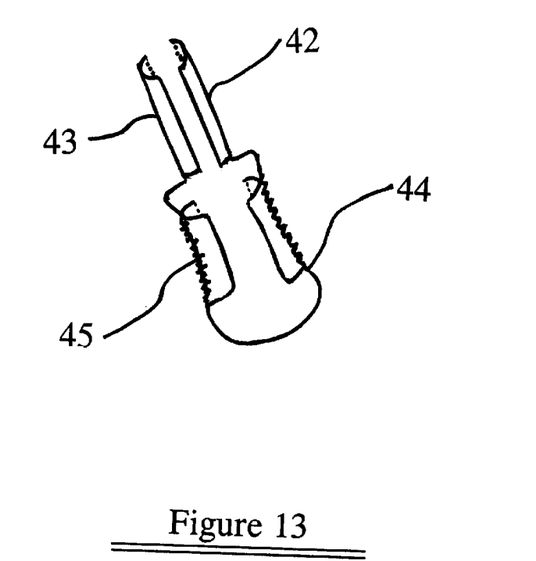
FIG. 13. This shows a delivery unit for the unit shown in previous figure of 12.

FIG. 13. This figure shows a delivery unit that is designed to be used in placement of the nasal unit shown in previous figure of 12. This is one means of delivering the nasal unit. This unit is basically made from a U shaped spring that has two arms of 42 & 43 which will fit and can be placed inside the tube 36 from the nasal unit shown in FIG. 12. The arms of the spring will separate from each other to hold the nasal unit in place. Then it will allow an uninflated nasal unit which naturally has smaller volume to be placed in the nostril over the bleeding area, then to be inflated to press the mucosa and stop bleeding. After proper placement then the arms of this unit shown at FIG. 13 can be dislodged from the nasal unit by pressing the sides 44 and 45 of this delivery unit that has a proper shape and rough surface for a better grip. When the hands of the unit are released then the delivery unit can be easily moved out to leave the nasal unit in place. Many other methods may also be used for such a placement.

Figures 14, 14A:
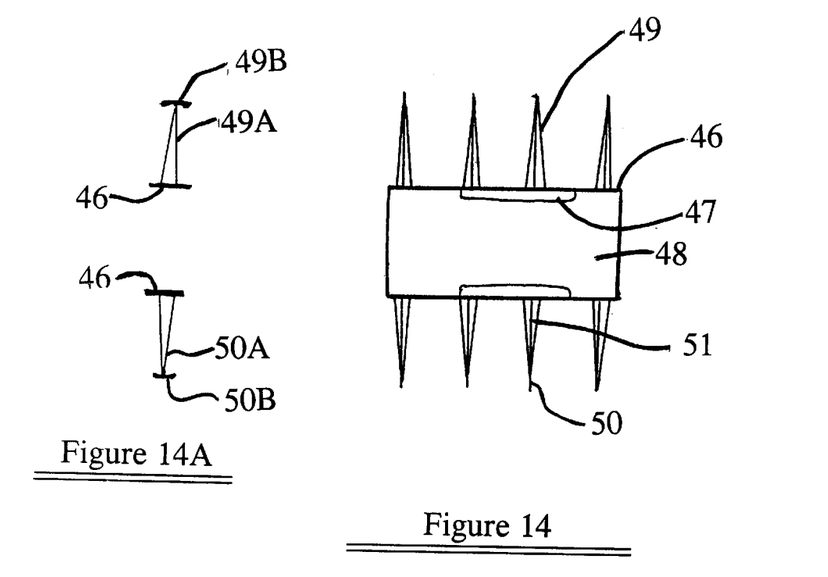
FIG. 14. This is a cross cut view of a unit that has walls in its outer surface instead of balloons.
FIG. 14A. This shows the outer rim of the walls of the units shown in FIG. 14 which is made to be flat soft plastic FIG. 15. This shows the side view of the unit shown in previous figure of 14.

FIG. 14. This figure is a cross cut view of another prototype unit similar to the one shown in previous figure of 1. Except in this unit instead of the balloon to block the area the unit has a series of soft walls 49–50 which they have a circular shape and will stand perpendicularly over the central tubing C shown at 46. These walls will occupy the inner space of the place such as colon and will act like a valve so that specially a series of those here four of them are shown will prevent from motion of the waste material downward.

The softness of these walls will allow them to be pressed during the peristalsis of the colon. Importantly the tip of them may be made flat (please notice no 49B and 50B from FIG. 14A) rather than being thin as shown in this figure. Here in this figure the cross cut of one of such valves are shown at 49–50 the figure also shows that this unit may have a wider base with a thicker center marked at 51 in order to provide more security and strength to the unit. The central tube C is shown at 46 and the inner balloon B is marked at 47, and the inflation tubing for the unit is not shown. The use of such units will be primarily to prevent from secretions to pour down during a procedure. The size, thickness, softness, width and the smoothness of surface and the other characteristics of the parts or the whole of this unit may vary from one model to the other one.

FIG. 14A. This figure is added to show how the outer rim or border of the walls of the units shown in FIG. 14 may be made to be from a flat soft plastic rather than being thin as shown in figure of 14. Here in this figure a small piece of central tubing 46 is shown with one wall of 49A–50A on its outer surface. However the outer rim of this wall is covered by a rather flat soft plastic here shown at 49B and 50B. In order to provide more contact with the inner wall of the space which they are located. The size, thickness, softness , width and the smoothness of surface and the other characteristics of this part and the whole unit may vary from one model to the other one.

Figure 15:
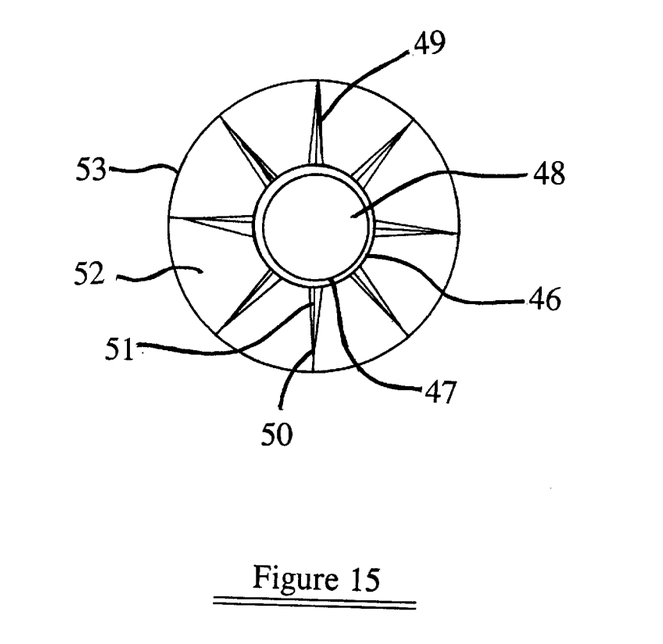

FIG. 15. This figure shows the side view of the unit shown in previous figure of 14. In this figure the central tubing C is marked at 46 and the inner balloon B at 47 and in deflated state. One of the circular valves are shown at 52 with its outer border at 53 and the 49–50 to show the part that are like a series of poles in center of this wall for giving more strength and body to the valve this part has a wider base with a thicker center marked at 51 in order to provide more body, and stability and strength to the unit. Importantly the number of these pieces or poles may vary from model to model and there can be many of them in order to give more body to unit. The inner open space of 48 is shown as well.

Figure 16:
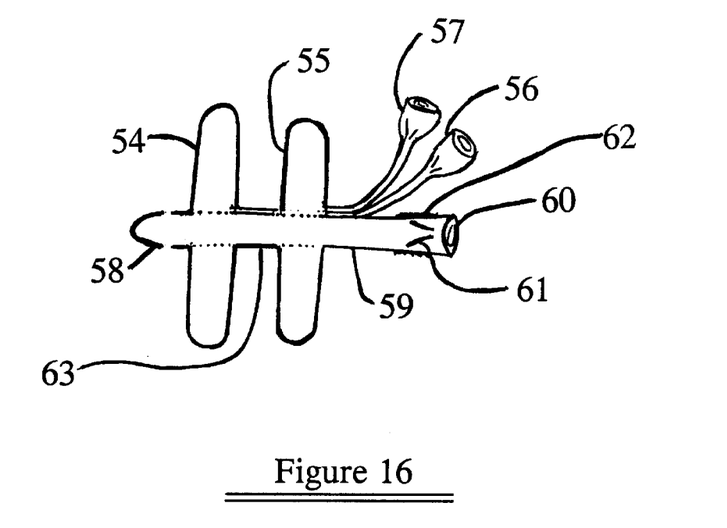
FIG. 16. This shows a cross cut view of a unit designed to be used in incontinent ladies FIG. 17. This shows a cross cut view of a unit to be used in incontinent patients FIG. 18. This shows a unit that also has a soft tubing in the rear rim of the central tubing C FIG. 19. This shows a unit for stopping bleeding in the rear and front of the nose.

FIG. 16. This figure shows a cross cut view of a special model of these units that is designed to be used in incontinent ladies and to be placed inside their bladder to prevent from uncontrolled drainage of the urine. This model has two balloons of 54 and 55 that the balloon 54 is to be placed inside the bladder adjacent to the opening of the urethra and the balloon 55 is to be placed outside of the bladder adjacent to the outer opening of the urethra so that these two balloons will hold the soft tube or catheter of 59–63 in place securely. This piece of catheter may be made from latex similar to regular catheters for bladder. The part shown at 63 to be in the urethra of the patient and to allow the unit to drain the urine out of bladder from its opening in the sides of the tip of the catheter 58. The urine will be poured out from the outer opening of 60 and the valve 61 will allow it to be done in convenient time. This valve may be made to be of a kind that with squeeze of its sides shown at 62 (these spots will be roughened to allow easy grip and handling) it will open and allow the urine to be leave the bladder and drain. Also any other proper valves may be used as well. The balloons will be inflated by the proper openings of 56 and 57 as well. The size, thickness, softness, width and the smoothness of surface and the other characteristics of this part and the whole unit may vary from one model to another to make a unit to fit one particular use.

Figure 17:
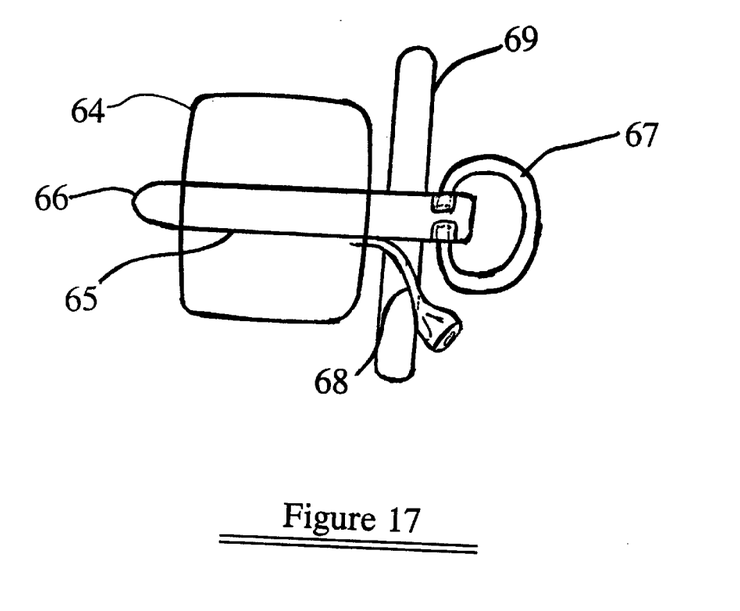

FIG. 17. This figure shows a cross cut view of a special modified model of these units that is designed to be used in conditions such as incontinent patients who can not control their bowels or in cases such as colostomies that a mean of control is needed at least in certain short occasions. This unit will consist a balloon no 64 that will be placed inside the bowel in an uninflated condition by inserting the round tip of 66 from its body 65 so that it can be easily placed inside the rectum or bowel of the patient then the balloon 64 will be inflated via the tubing 68 to close the inner space of the bowel. The outer balloon 69 will be also inflated or may be already inflated to prevent from the unit to move inside and cause problem. The handle 67 will allow a convenient control of the unit and it will be turned to the side after placement. The center piece 65 of this unit may be solid or to be open to allow the passage of the gas to occur. The size and relative size and any other important components and characteristics of this unit may change from one model to another to make a unit to fit one particular use.

Figure 18:
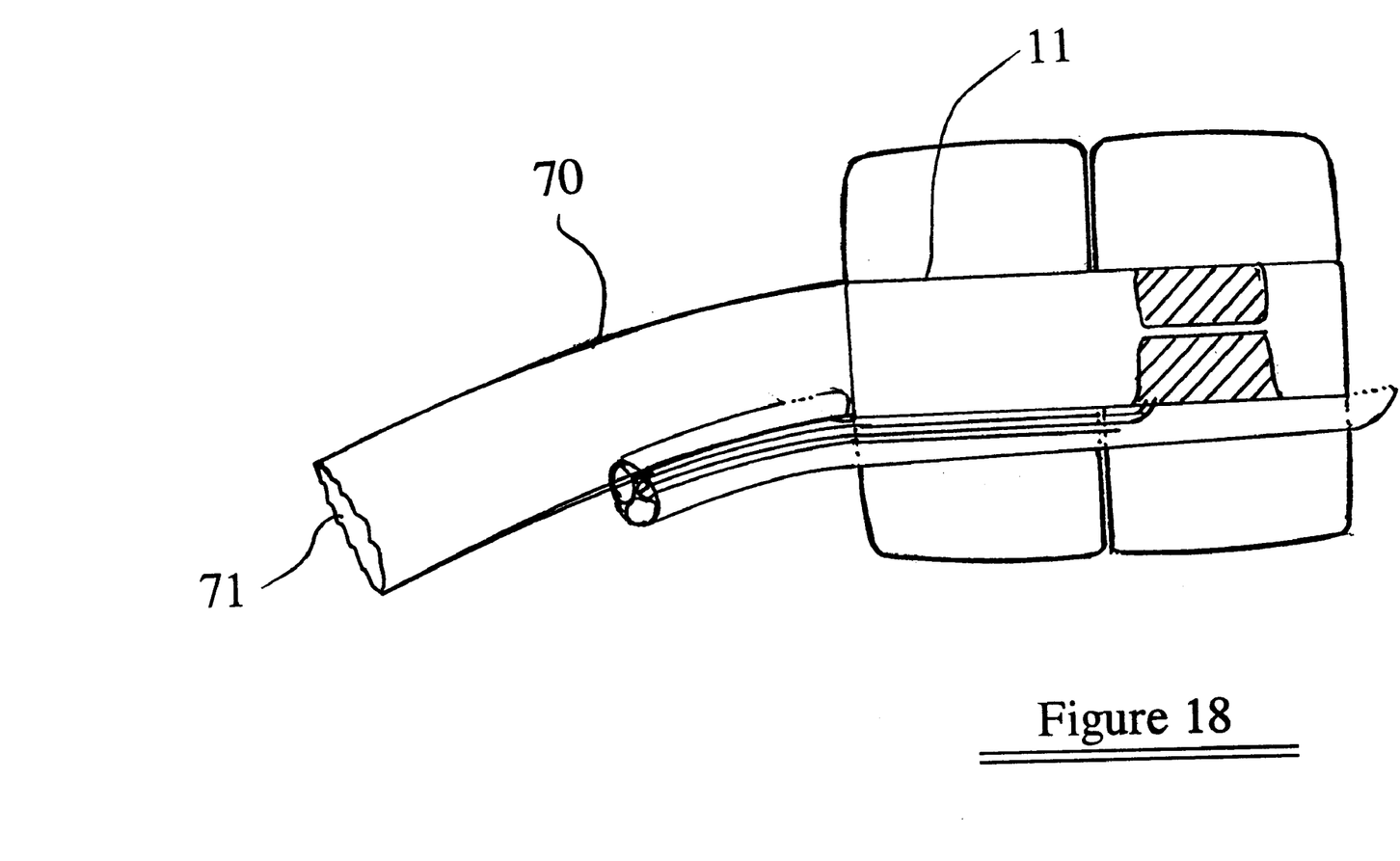

FIG. 18. This figure shows a cross-cut view of a model that is very similar to the units shown at FIG. 6 except this unit also has a soft tubing made from a clear non-sticking plastic shown here at 70 that is connected to the rear rim of the central tubing C of this unit here shown at 11. The benefit of this tubing is that is will allow the waste materials to move inside it without touching the inner surface of the colon. In this fig the opening of this tube is shown at 71; however, only the beginning part of this tube is shown due to the lack of space, however it will be long enough to reach the rectum. Importantly, this plastic cover will also function to cover the shaft of the scope and prevent it from touching the patient's colon. The other end of this unit may also have similar cover as well if it was thought to be needed.

Figure 19:
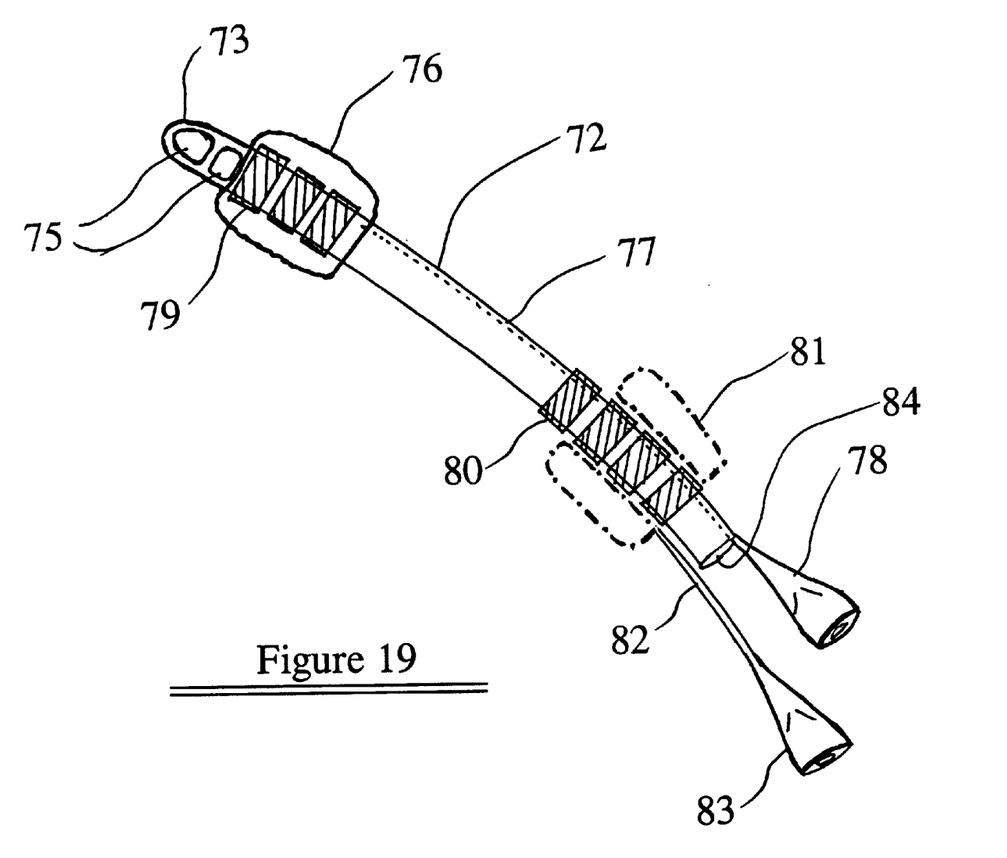

FIG. 19. This figure is to schematically show a unit that is to be used for stopping bleeding in the rear side of the nose as well as the front simultaneously. This unit has an inner tubing that is shown at 72 and will be made from a soft material such as latex. However, the wall of this unit will have rings of rigid material (here shown in dashed lines and marked at 79 and 80) which will be separate from each other and will prevent the collapse of the center tubing under pressure from inflated balloons. This central tube has openings in its tip shown at 75 that will allow the motion of the air. This unit has one balloon in its front part marked at 76 that will be inflated by its opening shown at 78. and it will stand in the rear opening of the nose. Another balloon shown at 81 will slide over the lower side of the tubing to be positioned in the nostril area. This lower balloon will be inflated by tubing 82 and opening 83. the opening of the tubing is shown at 84.

Figure 20:
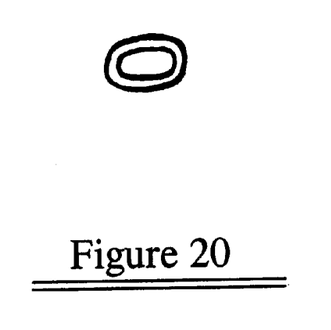
FIG. 20. This figure is to show that the tubing 72 can be flat.

FIG. 20. This figure is to show that the tubing 72 can be flat.

THE DETAILED EXPLANATION OF THIS INVENTION

The human body is a strange unit, very meticulously made and complex as well. The organs and their functions are amazing and delicate as well so that a disturbance in their function may cause significant problems in other parts of the body and therefore should be avoided. However, some problems in the humans are common such as bleeding in many different hollow areas such as the nose, stomach, bowels, uterus, bladder etc. Also infections, ulcerations, growths and surgeries in these areas occur and have to be handled and taken care of. But importantly, many times the openings of these areas should not be blocked, since the function of these parts are vital or important to the whole body and should not be disturbed as much as possible. Take the example of nasal bleeding. In this problem commonly the nose is packed by a medicated gauze to prevent from bleeding. However the blockage of the nose is problematic, disturbing and uncomfortable—the person will have a hard time breathing and will suffer until it is removed. In another part of the body, as in the large bowel, the person may bleed due to ulcerations, diverticular disease etc. And so far there has not been a good suggestion for this treatment, that the inventor is aware of. So in this vacuum he suggests a method and means of using special balloons to be inflated and prevent such a problem. However the inflated balloons alone would be problematic in this area since an inflated balloon will prevent the passage of gas and waste materials in that area and the person will be in trouble. Also the transportation and delivery of these balloons to the needed area are not easy as well and need a technique. For these reasons a solution is suggested by this inventor and that is to make a special balloon here referred as D. Balloons which are units to be used in these conditions. Basically, these balloons will be inflated to occupy a hollow part of the body and prevent problems while their inner opening would allow at least partial function of the area to be continued. What this inventor proposes is to make a soft balloon that will have a proper construction and shape and capacity in order to match the shape and size of the area of use after inflation. So naturally the shape and size of this balloon will be different from one unit used in one area from the other model that will be used in another area. For example in the nose it will have a size and shape of the part of the nose it will be used; in the stomach or the duodenum it will have the size and shape of the area and in the colon it will have the shape and size of the colon that it is to be used and may even have a different shape and size for different parts of the colon. This unit however, is also to have a proper opening in its center or body in order to allow the passage of air or the other materials that commonly go through that part to occur as well as medication and treatment means that are needed to pass through as well. For example in the nose it is important to allow air to pass through the unit and the person to breath, in the esophagus it is important to allow the food to pass through for the body to be fed and in the colon the waste material and gas to pass and not to cause trouble. So while different models of this unit will be made for different parts and areas of the body, they all will share the same basic idea with some modifications.

The balloon for gastro-intestinal system

In the gastro-intestinal system this balloon will have a significant role to play. In order to give an example of a useful model a prototype will be explained for the colon and its use and specifics will be explained. Then it will be easy to conclude how similar units may be also made to be used in the other parts of the gastro-intestinal system as well as in the other parts of the body.

The unit for the colon

Basically, the unit for the colon will have many uses. One of them is the prevention of bleeding. Bleeding in the gastro-intestinal system and colon occurs for many reasons such as ulceration, inflammation, rupture of a vessel, after removal of polyp etc. And in general it is something that should be avoided and prevented since otherwise the patient life will be in danger—he would need to be transfused, operated etc. All of these are costly and sometimes risky as well. Therefore, if a non-invasive method could be used it will be of significant value, particularly since in many cases, simple techniques such as pressure to the bleeding spot may be enough to stop bleeding and allow the body's own protective methods to function and prevent further bleeding. Therefore such measures can be very helpful and lifesaving, considering the fact that many other methods of treatments such as surgery are simply not available everywhere and all the time. Therefore even if the units mentioned here could temporarily prevent from problem and bleeding for short periods of time, still it will be very useful since the amount of blood loss will be less and it will give the proper chance to stabilize the patient for surgery or take him to a center that is equipped for surgery, since not all of the emergency centers that these patients have been seen for first time are equipped for surgery. Also if this unit could prevent the loss of blood from ulceration of stomach, bowel or colon and related transfusion of only one unit of blood it would have caused significant saving and complications.

This unit has other uses as well; for example, during the colonoscopy it may prove to be very valuable unit in allowing better vision, since during colonoscopy and similar procedures a clean area for proper vision is necessary in order to see the underling mucosa and possible problems such as polyps, ulcerations etc. However, the continuous pouring of the waste materials and secretions coming from upper bowels cause a problem and prevent from clear vision. In these circumstances and during such procedures many cleaning efforts need to be done which are time consuming and at times not effective as well. However this inventor believes that in those conditions the placement of the such a balloon in the upper colon will be of help in order to block the draining of the waste material from above so that the cleaning of the lower area could be done by flushing water. Then the clean area will allow better vision for better and more accurate results. In other words the balloon may be used to occlude the large bowel temporarily and prevent secretions to come until the procedure is over. This may be also used during certain GI surgeries as well to benefit from keeping the area clean or medicated. For this purpose simpler balloons may be enough.

For this use a properly sized balloon in the shape of a cylinder or a similar shape will be used. This will be made from a soft material that after inflation could and would assume the shape of the colon in the part of use. This unit will have a tubular rather rigid central part (here may be referred as central tube C.) that would give shape and body to this unit and allow it to be mounted on the tip of scopes or any other carrier that will be used to take this unit to the right place. The inner surface of this unit may have a balloon (may be referred as balloon B, compared to the outer balloon referred as the balloon A) as well as to close the inner opening of this unit after its inflammation and to hold it in the tip of the scope tightly. First the balloon will be placed in the tip of scope by having the tip of the scope to pass through the inside of the central tube C. Then the balloon B will be inflated to tighten and to hold the tip of the scope inside itself and to carry it. This will allow the balloon to be carried to the right place by the motion of the tip of the scope. Importantly the surface of the balloon B may be made to have a series of bumps or lines in order to give a better grip to it. Even the surface of the balloon A may be made to have a series of bumps or lines in order to give better contact to it as well. Or it may have a series of short walls to produce such a construction. After delivery of the unit and when the balloon system is to be left in a particular place then the balloon A will be inflated to get larger and to stand in the area by touching the wall of the colon. At this point the balloon B will be deflated to release the shaft of the scope so that it could move inside the unit easily up and down. After the scope is pulled out then the balloon B may be inflated again in order to close the opening of the unit.

Importantly this system may be enhanced by adding one or more tubes in it as follows:

a. One of these tubes may be used in order to flush the water to the colonic space above the balloon. This will be useful in many ways such as to liquidate the waste material above the balloon (no 6 FIG. 1) if they happened to be solid and to make them looser to come through the center opening of the balloon system to prevent from blockage.

b. A second tubing may be included to be part of the unit in order to have an opening before the balloon system (no 5 FIG. 1) in order to allow flushing the water in the colonic space below the balloon. This will be useful in flushing and cleaning the colonic space proximal to the balloon system for better visualization and liquidation of the waste material below the balloon for a better removal and vision.

c. A third tubing (not shown in pictures) may also be used in certain models to allow placement of certain wires or control cables for special usages such as manipulation and removal of the waste material, as well as helping in manipulation and moving this unit along the colon in certain cases. These tubes may allow a wire that has the capacity of manipulated to be inserted inside it to allow adjustment of this unit to be done inside the colon. Some means of these kinds of controls can be done with the insertion and use of a remote control wire that can be manipulated from the body to change the direction and bent of their tip. These wires will be inserted inside a proper tubing in order to allow the unit to be controlled and the movement and placement of the unit to be done. Alternatively the balloon may have a remote controlable wiring system inside the tubing to allow the adjustment and manipulation of its tip for positioning to be done from outside.

When the unit is in proper place, then the outer balloons of it will be inflated to fill the area and part of the colon that it is placed inside it, so that it will occupy the space of the colon and the outer wall of the balloon will be against the wall of the colon and it will press the wall and prevent from bleeding or to provide medication and movement of the materials in this area. Then the center opening of this unit will allow the passage of the waste materials to be done if it is deemed to be necessary. Alternatively with the inflation of the balloon B, the inner opening of the unit will also be closed to prevent motion of the waste material downward for any reason that the user decides. For example during colonoscopy, naturally the examiner wishes to see the area in a clean condition, but the continuous drainage of the materials from the bowel above interferes with such job. And there has been cases that after cutting a polyp it was fallen inside the fecal materials and not to be found to be tested. In such a circumstance, with the inflation of the balloon B it will prevent the draining of materials beyond this unit and this will allow the examiner to visualize the area more clearly and to flush and clean the lower area more thoroughly . And importantly one model of this unit may be made to allow the biopsy specimen to be accumulated inside it and to prevent it from being lost.

These balloons can be mounted to the tip of the scopes such as Gastroscopes, Colonoscopes or similar units by some other means as well such as snaps or tape, etc. Even newer models of such scopes may be made having a means of accepting and holding and delivery of such balloons and means in place. These means will allow the placement of these balloons on the tip of the scopes or somewhere in its body to occur and then to be released later when it is needed. The connection may be also made by a piece of adhesive tape or a glue to be released after inflation of the main balloon, or a balloon made for such purpose.

These units may have different models to help in different needs or they may be fortified by some more features for example A. The unit may be made to consist from combinations of balloons so that it will allow one of a series of them to be deflated while the other ones will be inflated to allow an alternative inflation.

B. The unit may have a soft plastic tubing connected around the central tubbing C that will carry the waste material from the center tubing C to the anal area so that the area of the colon under the balloon will be spared and would not be contaminated by the waste material.

C. The balloon may have a shape similar to the one shown at FIG. 9 so that it will allow the waste material to move through the empty space, so the areas of the wall of the colon that need to be pressed would be pressed.

D. The center tubing C of this unit may be made to be flexible, so that it could bend when necessary. This will allow the units to be placed in bent areas of the colon or to be placed in the side of the scope that will bend during its turn along the colon.

E. The unit can be made to be clear to allow vision to occur.

F. The surface of the unit may be made to have a cover such as a gauze which can have medications in/on it so that the medication can be delivered to one particular area of the colon. Among the medications, local anesthetics, antibiotics, anticoagulants, anti-inflammatory agents are of prime interest although any other medications may be used as well.

G. The unit may have a small motor in it to allow it to be moved along a dented string up and done. This can be done when the engine has a turning wheel that stands and holds the string and with its rotation will move the unit up or down on the string. Such a unit can be separate from the balloon and to move on the tubing of the balloon or event a unit may move on the shaft of the scope as well.

H. The unit may be also made to carry a small camera in order to allow it to take pictures from different parts of the colon for different purposes.

I. The unit may carry a fiber-optic lines connected to a proper lensing with itself to allow the view to be seen.

J. The unit may have a light to allow vision to occur. Also this light will allow the position of the unit to be noted inside the abdomen by searching for light in a dark room or under a proper cover.

K. The light of unit may be chosen to be therapeutic with using lights that may have special effect in the tissue. Such as ultra violet light etc.

L. The unit may be used to deliver radium or any other similar material in order to allow a particular growth in the colon to be handled and such medications to be delivered locally.

M. This unit will be made to be Radio opaque by having preferably the central tubing to be radio-opaque in order for the position of the unit in the body to be verified by the X ray.

N. The unit may be made to have more than one unit so that one of them will be placed in one area and another one to be placed in another place of it.

O. The length of the unit will vary so that a long unit may be used for a long part of the colon for different reason such as the application of pressure or medication in a long part of colon.

P. Units will be made for the vagina in order to allow it to be inflated to prevent from bleeding or other purposes such as application of medications.

Q. A unit to be made to have a long sleeve in order to cover the scope beyond the balloon.

This unit may be made to move up and down over a cable or even over the shaft of the scopes. The means of this motion will be a small engine that will cause the motion of a series of wheels that will rotate on the cable or the scope in order to move it up and down on the cable or body of scope. There may be only two wheels, one on each side of the cable or scope in opposite sides. This move will allow the means of flushing as well as the biopsy or snaring to be taken and to allow a better job to be done. The cable may have a series of dents that will allow the wheel to move better. The moving wheel can be operated by electricity run through a wire to energize an engine to move the wheels and the wheels to move the balloon up.

One model of this unit will be made to have a clear plastic tubing X connected to it from the sides of the central tubing C down (as shown in FIG. 18) and it may be of help in delivering medication to the wall of the colon in a concentrated and undiluted way that otherwise may not be achieved. For example in ulcerative colitis the medication may be injected between a plastic tubing X and the inner surface of the colon and in this model the lumen inside the plastic tubing X will carry the waste material out and prevent it to touch the surface of the colon. This technique would need some more study in different conditions to prove whether it will be beneficial.

However it opens a new possibility that gives some hope. importantly, in order to make the balloons bend without loosing their function, their inner tubings may be flexible, similar to the body of an accordion (please notice FIG. 10) and also the balloons may be made from combinations of balloons to allow the bending of the balloon to occur as well. Alternatively the center tubing C may be made from combinations of separate parts or pieces that will be connected to each other by plastic or balloon and will allow bending of the balloon to occur. Importantly here again the balloon may be made from combinations of different balloons as well to allow bending to occur. Such a model was shown in FIG. 11. Many other modified models may also be made to do the same job and allow the unit to bend as well. The size and length of this unit may vary and a long unit may fill a good part of the colon in order to decrease the chance of focal pressure and perforation and to allow the application of pressure to be done. So importantly, this unit may be made from combinations of a series of the balloons for different purposes as well.

Importantly in some models the unit may be made to have soft sponge in its outer layer instead of balloon. These sponges are to have the proper size and shaping to occupy the space of the colon between the inner surface of the colon and outer surface of the central tube C. The outer surface of these sponges may be chosen to be absorbent or non-absorbent. The sponges not only will be used in models for the colon but also in any other models. The size, shape, thickness, consistency and other characteristics of these sponges may vary significantly from model to model.

Importantly in some models, the units may be made from combinations of balloons and the soft sponges as well. For example, a layer of soft sponge may be used to cover the outer surface of the balloons A so that with the inflation of the balloon the size of the unit will be large and would occupy the space that is used. In this condition the outer surface of the sponge will touch and press the inner surface of the space they are used. Again, the outer surface of these sponges may be absorbent or non-absorbent. These sponges may be chosen to be saturated or be covered with different medications and allow them to be used on the inner surface of the colon or the space. The use of the sponges will be not only in models for the colon but also in any other areas that they can be useful. The size, shape, thickness, consistency and all of the other important characteristics of these sponges, balloons and all other components of these units may vary significantly from model to model.

Importantly in some models a series of circular walls, flaps or wings may be used to stand around the central tubing C of unit as shown in FIG. 14 and 15. so that these walls will act like a valve to prevent the secretions and waste material from moving down. The inventor believes that a series of these walls will be functional enough in certain cases to prevent the drainage of the waste materials inside the bowel. However, even in these models it may still be helpful or necessary to have the inner balloon B in order to allow the unit to be fixed on the tip of the scope or to take it to the proper place. The prototype of such units is shown in FIG. 14. Basically these units will have a series of soft walls 49–50 which will have a circular shape and will stand perpendicularly over the central tubing C shown at 46. These walls are to occupy the inner space that they are to be used in such as the colon or any other space and will act like a valve so that specially when a series of those are functional the unit will prevent the motion of waste material downward. The softness, design and construction of these walls will allow them to be pressed during the persitalsis of the colon and then to assume their shape. Importantly these walls may be fixed or may be moveable over the central tubing C. Also Importantly the tip or the outer edge of these walls may be made flat rather than being thin as shown in FIG. 14A no 49B and 50B in order to hold in the area better. The FIG. 15. shows the side view of such unit and the circular shape of its wall.

Importantly the tip of the scopes of the gastroscope or colonoscope or similar scopes may be modified in order to accept and carry and utilize these units easier.

The basic information and models shown here can be easily modified in order to make other models that can be used in the other parts of the body such as the stomach, duodenum, small bowel, esophagus, trachea and bronchi, etc to allow its beneficial effects to be utilized in those areas in any useful means and condition. This unit will be modified to be used in problems and ulceration and diseases of the stomach, lower esophagus or in duodenum or any similar areas. The inflation of properly made balloons can prevent from bleeding in those areas also Importantly this inventor suggests that it may be possible to apply a patch of medication over the ulcerated area to pack the ulcer area with it and keep in place by the pressure of these units to speed the recovery and healing and prevent complications. Even in the perforation of ulcer, duodenum or stomach it may be possible to use one model of such units with properly shaped and sized balloons in the area to prevent bleeding and also importantly to prevent from the materials inside the gastrointestinal system to leave out and cause their very imitative and damaging effects inside the abdomen.

Also this inventor has suggested to one of his patients (Mr Jer. Web this is a shortened name) who is morbidly obese to be treated by a large double balloon in order to have the large balloon inflated inside his stomach and to occupy the stomach space and prevent him to consume a large amount of food he eats usually in order to possibly prevent from the very poor outcome of such morbidly obese patients. (a letter suggesting this method was mailed to his physician in University of Michigan in Ann Arbor)

The unit for the nose=Nasal unit.

These units are to be used for the prevention of bleeding in the nose. Primarily they will be made in two different models: one for the front part of the nose and other one for the rear part of the nose in order to allow the bleeding to be prevented in these different areas. Combination uses of these parts may be possible in some cases as well.

The unit for the front part of the nose:

This unit will be made from a soft balloon that is able to assume the shape and anatomy of the front part of the nose in nostril area after inflation. It will be placed in the area in a deflated condition easily; then it would be inflated to assume the shape of the area and to press the walls and mucosa of the nose in that area to prevent bleeding. Some models of this unit may have a handle to allow easy and comfortable placement in the area and this handle can be cut after use, or it may use a delivery system similar to the one shown in FIG. 13. Importantly this unit will also have a rather rigid tubing in its center that will allow the air to pass through for breathing. This rigid center piece no 36 from FIG. 12 will also give body and allow the unit to be placed in the area as well. The tip of this piece will be made curve shaped as not to cause damage inside the nose. The balloon of this unit will have an inflation port that will allow it to be inflated by a bulb or a syringe. And it will have a valve that will prevent the air to move out unwantedly. This valve can be of any proper kind; however preferably it can be of a kind that will allow the inflation of the balloon by syringe during the connection of the syringe and then to close after the syringe is removed. This unit may be covered by certain medication such as local anesthetics, lubricants and ointments of different nature, local antibiotics, etc. to deliver one favorable result or another by this unit. Importantly in some models of this unit a soft sponge may be used instead of the balloon. These sponges are to occupy the space of the nose and their outer surface may be chosen to be absorbent or non-absorbent as well. These sponges may be saturated with medication of one sort or another. Also in some models such units may be made from combinations of balloons and soft sponges as well. For example a layer of soft sponge may be combined to cover the outer surface of the balloon so that with the inflation of the balloon the unit will enlarge and occupy the space of the nostril and close it while the air still can move through the inner open tubing. The outer surface of these sponges may be absorbent or non-absorbent. These sponges may also be saturated or be covered with different medications as well. The size, shape, thickness, consistency and other characteristics of these sponges as well as the balloons and other components of these units may vary significantly from model to model.

The unit for the rear part of the nose. For the rear part of the nose the same principle will also be used—basically the unit (show at FIG. 19) will be made from a central tubing that may be made from latex with a rigid areas such as rings (no 79 and 80 FIG. 19) under the balloon so that the inflation of the balloon will not close the central opening of this tubing. The rest of the tubing may also have some pieces of rigid plastic as well to prevent the collapse of the tubing. The tip of this tubing will have a soft balloon (76 FIG. 19) with a basic shape of the rear part of the nose, specially to be able to accept the shape of the place after inflation. This unit will be pushed into the area from the front part of the nose and into the rear part of the nose, in its open area, and then to be inflated to occlude the area and stop bleeding due to the pressure applied. The rear end of the tubing of this unit will have openings (no 75 FIG. 19) to allow breathing. This balloon will have an inflation port (78 FIG. 19) to allow it to be inflated by a syringe or a similar unit, the end piece will also have valve in it. In one particular model of this unit the front portion of the unit will have a balloon (no 81 FIG. 19) as well to allow it to be placed in the front part of the nose and be inflated to prevent bleeding. Importantly the second balloon (no 81) could slide over the tubing to be moved up and down over the tubing of the unit so that it will allow it to be properly positioned in the front part inside the nose and then inflated. The advantage of this unit is that it will allow the patient to be able to breathe from the inner opening of this unit. These two units will close the front and the rear opening of the nose to prevent bleeding and its related complications.

Some other use of these units in gastro-intestinal system.

Another model of these double balloons may be made to prevent the uncontrolled motion of certain materials in some areas of the body. For example, a unit may be made to be used in incontinent ladies in order to prevent the uncontrolled draining of the urine. One prototype of such a unit is shown at FIG. 16. This special model has two balloons of 54 and 55 that the balloon 54 is to be placed inside the bladder and the balloon 55 is to be placed outside of the bladder very close and adjacent to the outer opening of the urethra so that these two balloons will hold the soft tube of 59–63 in place and its tubing (this tube may be made from latex and to be like the regular bladder catheters) shown at 63 to be in the urethra of the patient and to allow the unit to drain the urine out of bladder from its opening 58. The urine will be poured out from the outer opening of 60 and the valve 61 will allow it to be done in a convenient time and place. This valve may be made to be of a kind that with the squeezing of its sides shown at 62 (these will be properly shaped to give an easy grip) will open and drain, although any other proper valves may be used as well. The balloons will be inflated by the proper openings of 56 and 57 as well. The size, shape, thickness, consistency and other characteristics of these units may vary significantly from model to model.

Another special model of such double balloons can be also made to be used for the prevention of uncontrolled outpouring of the waste material from the bowels. This very embarrassing condition does occur in certain diseases and conditions such as old age, nerve-muscle malfunction in the anal area or in certain cases such as state post colostomies in which the release of the waste material is out of control of the patient and causes a very disturbing condition for the patient and families. In such conditions at times the person or the families may wish to prevent such an event at least on a temporary basis or for one particular occasion. For this purpose a unit is designed a prototype model of that is shown in FIG. 17. This figure shows a cross-cut view of a unit that has two balloons of 64 and 69 and the unit has a central piece of 65 that has a round tip of 66 so that it will allow the unit to be easily placed inside the rectum or the opening of the bowel of the patient in colostomy site. Then the balloon 64 will be inflated via the inflation tubing shown at 68 to close the inner space of the bowel. The outer balloon 69 may be precharged or it may be inflateable so that it will be inflated to prevent the unit from moving inside and causing problems. Importantly, the space between these two units will be far enough to stand in the sphincter area of the patient or in the opening of the bowel in the colostomy site and prevent the inflation of the inner balloon to dilate these areas and cause even more trouble. This unit will have a handle of 67 that will allow a convenient placement and control of the unit. The size, shape, thickness, consistency and other characteristics of these units may vary significantly from model to model to make a unit to fit one particular use.

Importantly, the usage of the models and the teaching of this application is not limited to human beings. When applicable, this may be used in animals as well. Also, even though the models are mentioned primarily for the gastro intestinal system, the use of this unit is not limited to this system. It may be also used in any other part of the body where it is useful, especially in the vascular system. Using the units in the vascular system allows blood circulation in the vessels to continue by using the technique mentioned in this application. These units will allow a special tube to be placed inside a vessel and to have its balloon inflated to prevent leakage of the blood outside. Instead of being put in a vessel, such a balloon may be placed inside a tissue as well to prevent from bleeding.

I claim:

1. A device for placement in a gastrointestinal tract to aid in procedural and therapeutci interventions of a gastrointestinal tract, said device comprising:

support tube means that is open at both a proximal end and at a distal end and that comprises wall means presenting a radially outer surface for facing a wall of a gastrointestinal tract and a radially inner surface opposite said radially outer surface;

outer annular inflatable balloon means disposed on said radially outer surface of said support tube means;

inner annular inflatable balloon means disposed on said radially inner surface of said support tube means;

said outer annular inflatable balloon means being radially outwardly expansible in response to inflation thereof and said inner annular inflatabale balloon means being radially inwardly expansible in response to inflation thereof, while said support tube means provides sufficient strength to resist radially inward collapse, when said outer annular inflatable balloon means is inflated and to resist radially outward expansion when said inner annular inflatable balloon means is inflated;

inflation means, including inflation tube means extending from both of said balloon means when both of said balloon means have been placed in a gastrointestinal tract, for inflating each of said balloon means to varying degrees of inflation independently of the degree of inflation of the other, including a set of inflation conditions comprising;

a first inflation condition wherein said inner balloon means is inflated sufficiently to expand radially inwardly to grip a placement means for placing both said balloon means in a gastrointestinal tract and said outer balloon means lacks sufficient inflation to impede the placement;

a second condition wherein said outer balloon means is inflated sufficiently to expand radially outwardly to contact a wall of a gastrointestinal tract while said inner balloon means remains gripping such a placement means;

a third condition wherein while said outer balloon means remains in contact with a wall of a gastrointestinal tract said inner balloon means is deflated sufficiently to allow withdrawal of such placement means without affecting the placement of said outer balloon means against a wall of a gastrointestinal tract; and a fourth condition wherein while said outer balloon means remains in contact with a wall of a gastrointestinal tract, said inner balloon means is inflated after withdrawal of such placement means sufficiently radially inwardly to substantially occlude passage of fluid through said support tube means.

2. A device for placement in a gastrointestinal tract to aid in procedural and therapeutic interventions of a gastrointestinal tract, said device comprising:

support tube means that is open at both a proximal end and at a distal end and that comprises wall means presenting a radially outer surface for facing a wall of a gastrointestinal tract and a radially inner surface opposite said radially outer surface;

outer annular inflatable balloon means disposed on said radially outer surface of said support tube means;

inner annular inflatable balloon means disposed on said radially inner surface of said support tube means said outer annular inflatable balloon means being radially outwardly expansible In response to inflation thereof and said inner annular inflatable balloon means being radially inwardly expansible in response to inflation thereof, while said support tube means provides sufficient strength to resist radially inward collapse when said outer annular inflatable balloon means is inflated and to resist radially outward expansion when said inner annular inflatable balloon means is inflated;

inflation means, including inflation tube means extending from both of said balloon means when both of said balloon means have been placed in a gastrointestinal tract, for inflating each of said balloon means to varying degrees of inflation independently of the degree of inflation of the other, including a set of inflation conditions comprising;

a first inflation condition wherein said inner balloon means is inflated sufficiently to expand radially inwardly to grip a placement means for placing both said balloon means in a gastrointestinal tract and said outer balloon means lacks sufficient inflation to impede the placement;

a second condition wherein said outer balloon means is inflated sufficiently to expand radially outwardly to contact a wall of a gastrointestinal tract while said inner balloon means remains gripping such a placement means;

a third condition wherein while said outer balloon means remains in contact with a wall of a gastrointestinal tract, said inner balloon means is deflated sufficiently to allow withdrawal of such placement means without affecting the placement of said outer balloon means against a wall of a gastrointestinal tract; and in which said outer balloon means comprises first and second balloons that are disposed side by side on said support tube means, one distal of the other.

3. A device as set forth in claim 2 in which said first and second balloons are independently inflatable on said support tube means, said second balloon is distal to said first balloon, and said inflation means alternately inflates said first and second balloons to maintain placement in a gastro-intestinal tract while avoiding continuous contact with a particular portion of a wall of a tract while such placement is maintained.

4. A device as set forth in claim 3 in which said second balloon has a proximal end that proximally overlaps a proximal end of said inner balloon means and a distal end that distally overlaps a distal end of said inner balloon means.

* * * * *